(12) United States Patent
Riley

(10) Patent No.: US 8,349,271 B2
(45) Date of Patent: *Jan. 8, 2013

(54) MEDICAL INSTRUMENT CONTAINER SYSTEM

(75) Inventor: Edward D. Riley, Falmouth, ME (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1543 days.

This patent is subject to a terminal disclaimer.

(21) Appl. No.: 11/369,428

(22) Filed: Mar. 7, 2006

(65) Prior Publication Data

US 2007/0212277 A1 Sep. 13, 2007

(51) Int. Cl.
*A61L 2/00* (2006.01)
*A61L 9/00* (2006.01)

(52) U.S. Cl. .......................... 422/300; 422/292; 422/297

(58) Field of Classification Search .................. 422/300, 422/292, 297; 220/491, 485, 185; 206/230, 206/485, 370, 363
See application file for complete search history.

(56) References Cited

U.S. PATENT DOCUMENTS

| | | | | |
|---|---|---|---|---|
| 1,840,561 A * | 1/1932 | Miller | ............................. | 220/810 |
| 3,704,906 A * | 12/1972 | Abercrombie | ................ | 292/247 |
| 4,157,145 A | 6/1979 | Jordan | | |
| 4,292,749 A * | 10/1981 | Thomas | ........................... | 40/308 |
| 4,478,344 A | 10/1984 | Rehrig | | |
| 4,834,125 A * | 5/1989 | Insalaco | ........................ | 134/201 |
| 4,887,747 A * | 12/1989 | Ostrowsky et al. | ........... | 222/556 |
| 5,384,103 A * | 1/1995 | Miller | ........................... | 422/310 |
| 5,424,048 A | 6/1995 | Riley | | |
| 5,540,901 A * | 7/1996 | Riley | ............................ | 422/300 |
| 5,660,784 A | 8/1997 | Cruce et al. | | |
| 5,681,539 A | 10/1997 | Riley | | |
| 5,840,261 A * | 11/1998 | Monch | .......................... | 422/300 |
| 5,918,740 A * | 7/1999 | Berry, Jr. | ...................... | 206/369 |
| 5,938,899 A | 8/1999 | Forand | | |
| 6,161,718 A * | 12/2000 | Monbo | ......................... | 220/486 |
| 6,193,932 B1 | 2/2001 | Wu et al. | | |
| 6,331,280 B1 | 12/2001 | Wood | | |
| 6,389,656 B1 * | 5/2002 | Pellikaan | ......................... | 24/326 |
| 6,599,482 B1 * | 7/2003 | Dorin et al. | ................... | 422/104 |
| D481,179 S * | 10/2003 | Wendt et al. | ..................... | D32/3 |
| 6,789,828 B1 * | 9/2004 | Borg | ............................ | 294/87.2 |
| 2002/0148763 A1 * | 10/2002 | Lutz et al. | ..................... | 210/232 |
| 2005/0019237 A1 * | 1/2005 | Riley | ............................. | 422/297 |
| 2005/0163686 A1 | 7/2005 | Bettenhausen et al. | | |
| 2007/0039904 A1 * | 2/2007 | Purushothaman | ........... | 211/41.8 |

OTHER PUBLICATIONS

Provisional U.S. Appl. No. 60/709,238.*
Ashwani Diagnostics: Medical and Surgical Equipment, http://www.ademcoindia.com/scientific-industrial-lab-equipment/autoclave/sterilizer-pressure.htm, Jan. 11, 2006.

* cited by examiner

*Primary Examiner* — Regina M. Yoo
(74) *Attorney, Agent, or Firm* — Hayes Soloway P.C.

(57) ABSTRACT

A container system for medical instruments comprising a molded plastic reticulated tray composed of a continuous rib that forms a tray rim and a plurality of intersecting ribs defining large openings therebetween. The intersecting ribs are dished and have opposite ends connected to the continuous ribs at spaced apart locations therealong. The plurality of intersecting ribs also have rounded surfaces so that a washing or cleaning fluid directed at the plurality of intersecting ribs from the outside, upon flowing through said openings will follow and intimately contact those rounded surfaces so that those surfaces are cleaned thoroughly. A preferred embodiment of the system also includes a reticulated cover releasably connected to the tray and various brackets for fixating instruments in the tray.

13 Claims, 6 Drawing Sheets

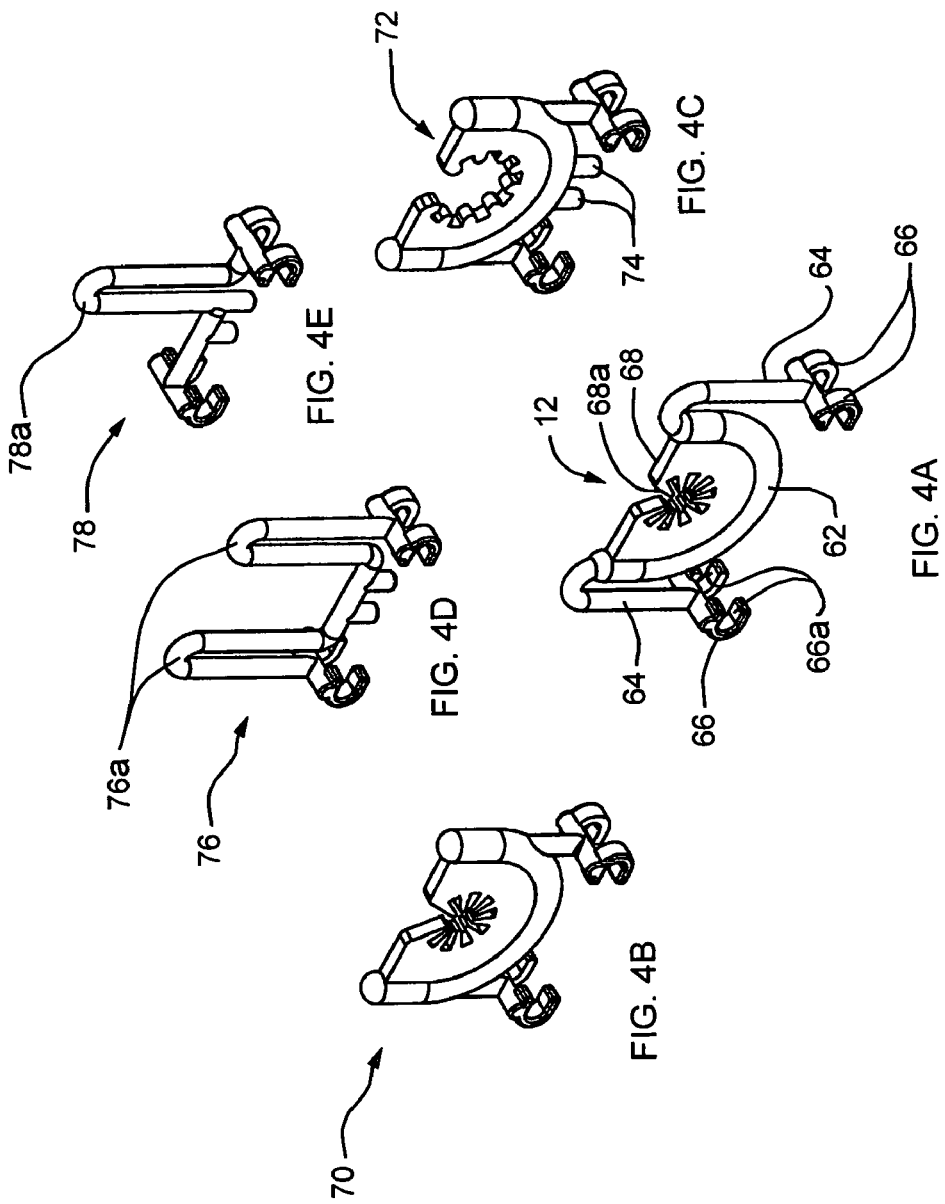

MEDICAL INSTRUMENT CONTAINER SYSTEM

BACKGROUND OF THE INVENTION

Field of the Invention

This invention relates to a system for holding selected medical instruments and devices during sterilization and storage prior to use and to facilitate their cleaning and storage following such use.

Different surgical procedures require the use of different sets of instruments or devices, the number of tools in the set depending upon the complexity of the procedure. Thus, prior to a particular procedure, the surgeon determines or knows from experience which instruments will be required. Those instruments are gathered together as a set, placed in a container which is packaged in a plastic package and sterilized in an autoclave. The packed instruments are then stored in that sterile condition until ready for use. When the surgeon is ready to perform the procedure, the container is brought to the operating room and opened, exposing the still sterile instruments therein. Following use, the instruments are usually returned to the container and sent to a cleaning facility where the containers and instruments therein are placed in a washing machine which directs jets of water/detergent cleaning fluid at the containers and their contents to clean them prior to resterilization.

To improve the circulation of cleaning fluid throughout the container, the container walls are usually formed with a multiplicity of vent holes which may be used to anchor the various brackets which support and fixate the various instruments within the container. Examples of such containers are disclosed in U.S. Pat. Nos. 5,424,048; 5,681,539; 6,193,932 and 6,331,280.

Heretofore, the various containers and trays used for the above purposes have been structures whose walls are more closed than open. In other words, the containers have planar walls with a multiplicity of vent holes therein leaving relatively wide webs of plastic extending between the vent holes, the total area of the webs invariably being much larger than the total area of the vent holes in order to maintain the structural integrity and rigidity of the container. As a result, when water/detergent or other cleaning fluid impinges upon the container during the cleaning process, the fluid may not come into intimate contact with all the inside surfaces of the webs with the result that those surfaces will not be cleaned to the extent that they should be. That is, as the cleaning fluid is directed into the container through the vent holes, turbulent flow occurs causing the fluid to flow past portions of the flat interior surfaces between the holes resulting in a shadow effect thereon and insufficient cleaning of the flat surface portions within those shadows.

In order to obtain a better circulation of cleaning fluid through the container during washing, it has been contemplated to use a more open structure for the container, i.e. one composed of intersecting ribs wherein the total area of the openings into the container between the ribs totals much more than that of the ribs bounding the openings. Thus it has been contemplated to form a tray or container of metal wire coated with a plastic material, i.e. similar to a dish washer rack. Although such an open structure composed of intersecting ribs allows maximum circulation of fluid through the container with minimal shadow effect, it is not particularly suitable for medical applications. This is because during normal usage over time, the plastic coating can be scratched or otherwise damaged exposing the underlying metal wire which will oxidize and provide sites for the buildup of bacteria. Also when such a wire structure is deformed, it will tend to remain so with the result that it may not inter-fit properly with other components of the container system. For example, if a wire tray is deformed, its cover may not fit properly on the tray.

Of course, the above problems can be avoided by molding the container or tray entirely of plastic as has been done for clothes baskets, soap dishes and the like. However, such molded plastic open structures are invariably constituted of intersecting webs or ribs which are thin and have a rectangular cross section. Resultantly, the containers of this type are not rigid enough to protect sensitive medical instruments. Also, since the inner and outer surfaces of those ribs are flat, they suffer the same shadow effect discussed above in connection with perforated plastic trays, albeit to a lesser extent. While the former problem can perhaps be alleviated by thickening the ribs, the latter problem cannot.

Thus it would be very advantageous if there existed a container for holding medical instruments during washing and cleaning processes which has the advantages of plastic coated metal wire baskets in terms of strength and rigidity and none of the aforesaid disadvantages thereof.

SUMMARY OF THE INVENTION

Accordingly, this invention aims to provide a medical instrument container system capable of protectively enclosing medical instruments while maximizing the exposure of the container interior to a cleaning fluid.

Another object of the invention is to provide such a system which includes a strong rigid instrument container in the form of a basket or cage molded entirely of a plastic able to withstand sterilization and cleaning processes.

A further object of the invention is to provide a system of this type which includes an instrument supporting basket or cage whose interior surfaces are shaped to minimize the shadow effect when a washing or cleaning fluid is incident on the basket or cage.

Still another object of the invention is to provide a medical instrument container system which includes a container and cooperating brackets capable of holding variously shaped instruments and devices in a variety of configurations within the container.

A further object of the invention is to provide a system of this type which can be made relatively inexpensively in quantity.

Briefly, my container system for medical instruments comprises a tray which is reticulated and molded entirely of a plastic material able to withstand washing and sterilization. The tray has relatively large openings bounded by ribs having cross-sectional shapes that round-off substantially all of the interior and exterior surfaces of the tray. Resultantly, when a cleaning fluid is directed at the tray from the outside, the fluid follows the rounded streamlined surfaces of the ribs through the openings to the inside of the tray thereby eliminating the shadow effect and ensuring that all interior surfaces of the container are intimately contacted by that fluid.

Each tray can be molded as a unitary part and thus can be made in quantity relatively inexpensively. The tray can be used by itself or fitted with a cover of similar reticulated construction. The cover may be releasably secured to the container to form a cage which protectively encloses the medical instruments without obstructing the free flow of cleaning fluid through the cage. As we shall see, my system may also include various instrument holders specially designed to be releasably secured to the ribs of the tray to fixate the instruments therein during handling prior to and following the cleaning process.

BRIEF DESCRIPTION OF THE DRAWINGS

For a fuller understanding of the nature and objects of the invention, reference should be made to the following detailed description taken in connection with the accompanying drawings, in which:

FIGS. 4A to 4E are perspective views showing various instrument holders that may be part of the FIG. 1 system;

DETAILED DESCRIPTION OF PREFERRED EMBODIMENTS

Figure 1:
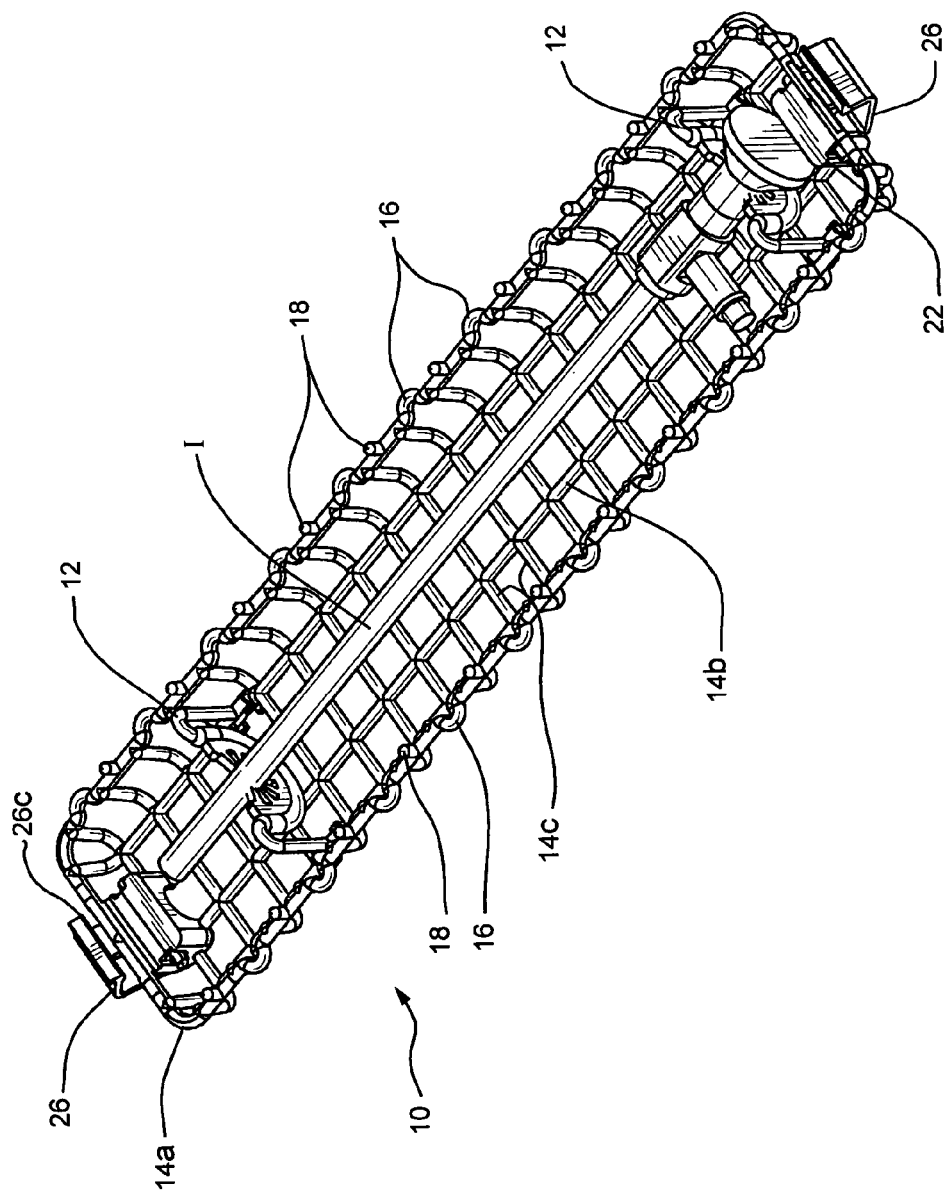
FIG. 1 is perspective view from above showing a medical instrument container system incorporating the invention.

Referring to FIG. 1 of the drawings, my container system comprises a tray 10 which may contain one or more medical instruments or devices I. While the illustrated tray is rectangular, it could just as well have some other shape, e.g. round or oval. Preferably, each instrument I is supported within the tray by one or more holders 12 which fix the position of the instrument within the tray.

Figure 2:
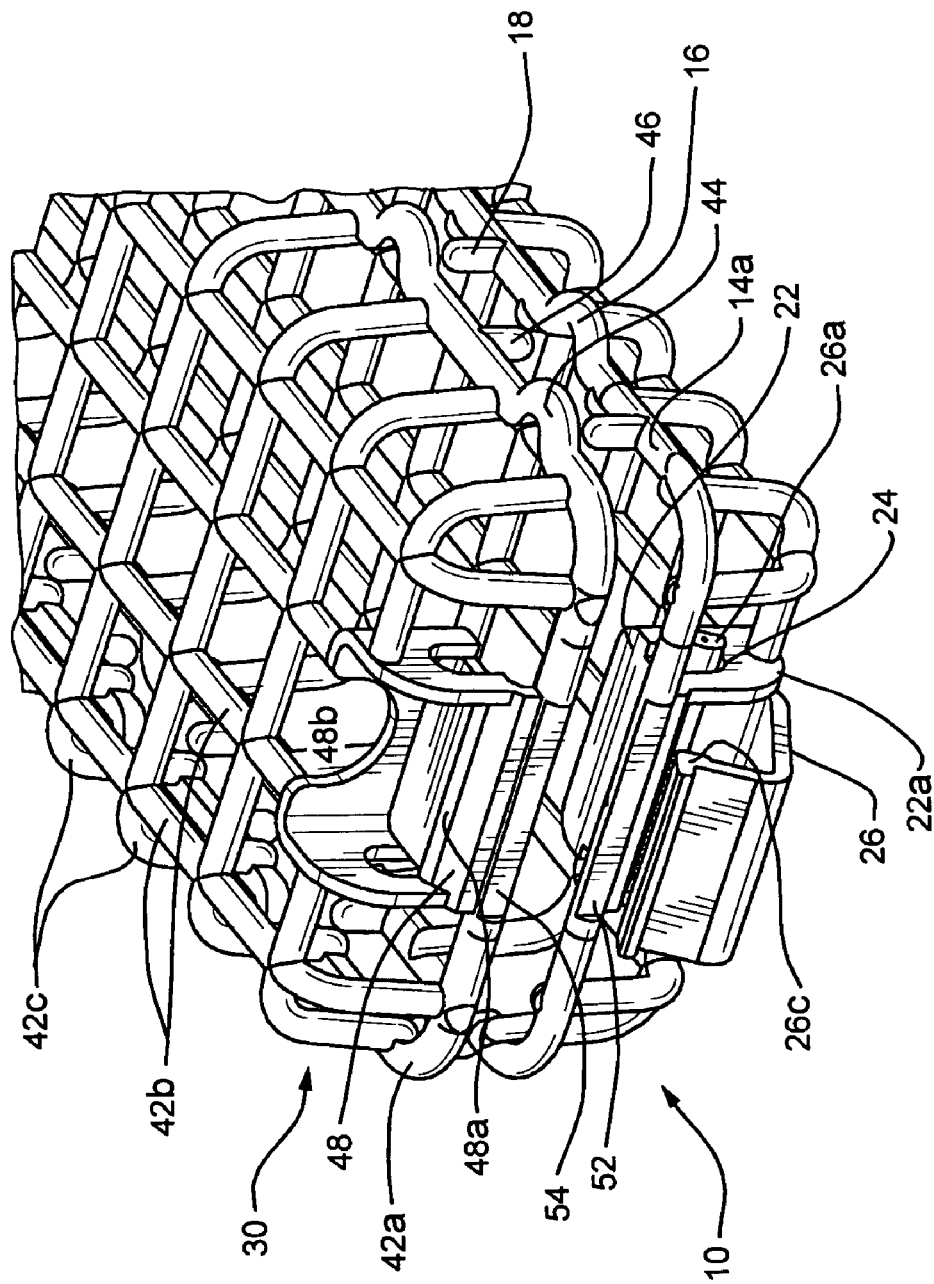
FIG. 2 is an exploded fragmentary perspective view on a larger scale showing the FIG. 1 system including a matching cover.

As shown in FIGS. 1 and 2, tray 10 is a reticulated structure molded entirely of a rigid plastic able to withstand cleaning and sterilization processes, e.g. polyphenylsulphone, PTFE, etc. Thus, tray 10 is composed of plurality of spaced-apart ribs. These ribs include a rectangular rib 14a which forms a hoop at the rim of the tray, a plurality of spaced-apart, parallel, longitudinal ribs 14b which comprise the bottom wall of the tray and a multiplicity of spaced-apart, parallel, transverse ribs 14c which intersect ribs 14b at the bottom of the tray. The opposite end segments of ribs 14b and 14c are bent up and connect to rib 14a at the inboard face of that rib at spaced-apart locations therealong. These segments form the sides and ends of the tray. Preferably, the ribs 14b and 14c are spaced an appreciable distance from their neighboring parallel ribs, e.g. 0.75 inch or more, so that the openings O between the ribs are quite large compared to the ribs. In a preferred tray embodiment, the total area of the tray openings O should be at least twice the total longitudinal sectional area of the tray ribs 14a, 14b. Also, the ribs are rounded, most preferably having circular cross-sections.

For reasons to be described later, the rectangular rib 14a is formed with a plurality of outward bends or loops 16 which are spaced along the length of that rib at the sides of the tray. Also, short locating pins 18 extend up from rib 14a between the loops 16.

Figure 3:
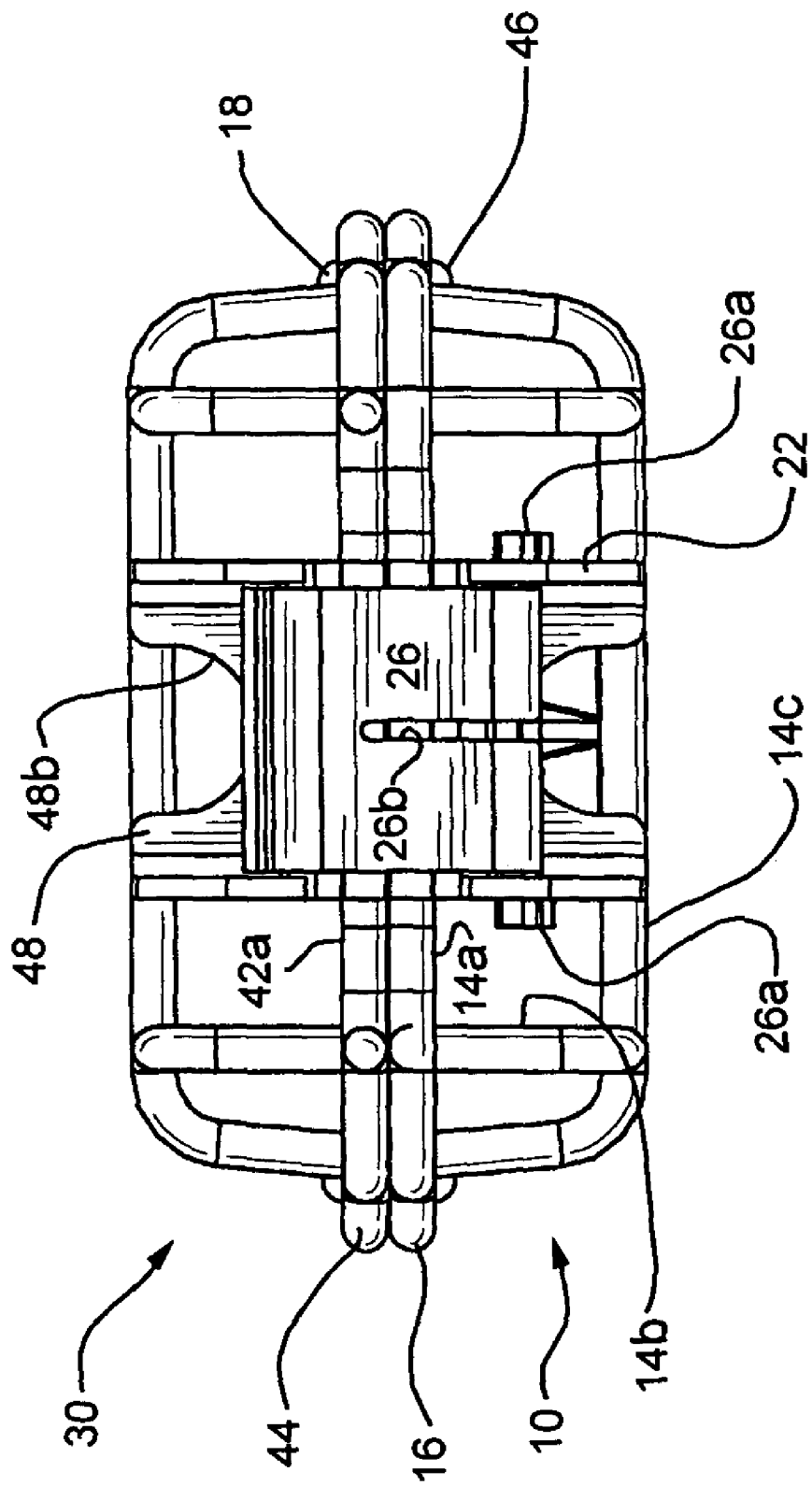
FIG. 3 is an end view of the FIG. 2 system in a fully assembled condition.

Attached to the ribs 14a to 14c at the opposite ends of container 10 is a pair of mirror image fixtures 22. Preferably, each fixture is molded integrally with the continuous ribs 14a and perhaps also ribs 14b and 14c. However, the fixture may also be designed as a separate part which can snap onto those ribs. Each fixture 22 includes a pair laterally spaced-apart ears 22a formed with holes 24 forming journal bearings for loosely receiving the laterally extending axles 26a of a latch member 26. As best seen in FIGS. 2 and 3, each latch member 26 is has a slit 26b between, and extending perpendicular to, its axles 26a so that the sides of the latch member may be pressed together to permit the insertion of the axles 26a into the holes 24 of the corresponding fixture 22 to facilitate the assembly of the latch members 26 to fixtures 22. When assembled, each latch member 26 may be swung between an open or unlatched position shown in FIGS. 1 and 2 wherein a latching surface 26c of the latch member 26 is spaced away from rib 14a of container 10 and a closed or latching position wherein the latching surface 26c is spaced above rib 14a a distance slightly less than the diameter of rib 14a.

Referring to FIGS. 2 and 3, preferably, but not necessarily, my container system also includes a mating molded plastic reticulated cover or lid 30. While the cover and tray may have different depths to minimize molding costs, the illustrated cover is more or less identical to tray 10 when the two are side by side and a mirror image when the cover is inverted as shown. Thus cover 30 includes a rectangular rib 42a similar to rib 14a and which overlies rib 14a when the cover is positioned on the tray as shown in FIG. 3. Cover 30 also includes a plurality of longitudinal ribs 42b similar to ribs 14b as well as a multiplicity of transverse ribs 42c comparable to ribs 14c and which intersect ribs 42b thereby forming the top wall of the cover. Ribs 42b and 42c are turned down at their opposite ends so that they connect to rib 42a at spaced-apart locations along that rim at the inboard side thereof.

As is the case with tray 10, the rib 42a which forms the rim of cover 30 is formed with a series of outward bends or loops 44 at spaced-apart locations at the sides of cover 30, as well as a series of locating pins 46 comparable to the pins 18 of tray 10. The respective locating pins and loops on tray 10 and cover 30 are positioned so that when the cover 30 is inverted and positioned on the tray, the locating pins 18 of the tray project up into the loops 44 of the cover and the locating pins 46 of the cover extend down into the loops 16 of the tray thereby maintaining the tray and cover in perfect register.

As best seen in FIGS. 2 and 3, cover 30 also includes integrally molded fixtures 48 at the opposite ends of the cover which are identical to the fixtures 22 of tray 10. However, they do not form hinges for the latch members. Rather, the fixtures 48 function as keepers for the latch members 26 when cover 30 is positioned on tray 10 and secured thereto by latch members 26. More particularly, each fixture 48 (as well as each fixture 22) is formed with a raised keeper surface 48a. When the corresponding latch member 26 is moved to its latching position shown in FIG. 3, the latching surface 26c of each latch member 26 resiliently engages and snaps over the keeper surface 48a of the corresponding fixture 48 thereby clamping cover 30 to tray 10. When so clamped together, those parts only make line contact along the ribs 14a and 42a, minimizing the likelihood of bacterial build up where the cover meets the tray.

It is obvious from the aforegoing that before assembly of the latch members 26 to tray 10, the cover 30 is identical to the tray. Therefore, those two parts can be made using the very same mold. The locating loops 16, 44 and locating pins 18, 46 are all positioned so that when the cover 30 is inverted and its rib 32a brought into register with the tray rib 14a, the pins 18 of the tray will project up into the loops 44 of the cover and the pins 36 of the cover will project down through the loops 16 of the tray. Furthermore, this applies for both end-to-end registrations of the cover with the tray. In other words, if the cover 30 is turned 180° relative to the tray, the various locating loops and pins will still inter-fit to bring the cover and tray into register.

As best seen in FIG. 3, to enable one to easily grasp the top of latch member 26 to pull the latch member away from the end of the cover to release the latch member from fixture 48, that fixture is formed with a finger notch 48b. Of course, a comparable notch is present in fixture 22 since the two fixtures 22 and 48 are identical. Also, to provide clearance for each latch member 26 when that member is swung to its latching position, the rim-forming ribs 14a and 42a may be provided with flats 52 and 54, respectively, which face the corresponding latch member as best seen in FIG. 2.

It is a feature of this invention that the molded plastic reticulated tray and cover construction described herein provides a container system which is strong and rigid and well able to protect the instruments in the tray. Yet, the container system is still very open in that the total longitudinal sectional area of the ribs is a relatively small percentage of the total area of the openings in the tray/cover. That coupled with the fact that the surfaces of the ribs are rounded, assures that a cleaning fluid directed toward the tray or cover will pass easily into and through those container components, following the streamlined contours of the ribs so that there is minimal or no shadow effect at the interior surfaces of the container. This ensures that the entire container system and its contents will be thoroughly washed or otherwise cleaned in a minimal amount of time.

Refer now to FIG. 4A which shows in greater detail one of the instrument holders 12 in FIG. 1. It is a molded plastic part consisting of a generally U-shaped base 62. The opposite ends of base 62 are turned outward and downward to form a pair of spaced-apart vertical legs 64 which extend down below base 62 and are terminated by a pair of mirror image clips 66. Each clip has one or more interior clamping surfaces 66a which are dimensioned to clamp to one or another of the tray ribs 14b, 14c. Molded integrally to base 62 is a flexible resilient instrument holding pad or portion 68 formed with an opening or slot 68a for resiliently receiving a medical instrument I as shown in FIG. 1. Preferably, the holding pad 68 is molded integrally with base 62 in the manner described in my pending U.S. application Ser. No. 11/299,505, the entire contents of which are hereby incorporated by reference herein. As described in that application, the holding portion 68 is molded integrally with the base 62 so that there are no interstices or crevices or openings between those members which could be possible sites for bacterial infestation.

As shown in FIG. 1, each holder 12 is clamped to the longitudinal ribs 14b at opposite sides of tray 10. Accordingly, holder 12 must extend substantially the full width of tray 10 to secure the holder to those outboard ribs 14b. To anchor the holder to the tray, the clip 66 at the end of one of the legs 64 is engaged to one rib 14b and the legs 64 are spread apart sufficiently so that the clip 66 on the other leg can engage the rib at the other side of the tray. Leg 64 are sufficiently resilient that when released, they return to unstressed positions which securely clamp holder 12 to the tray and maintain the holder's transverse position in the tray. While the illustrated clips 66 are flat metal parts, they may have circular cross-sections at clamping surfaces 66a where they contact the ribs to minimize the contact areas therewith.

Preferably also, the clips 66 are almost as wide as the distance between the transverse ribs 14c so that, when secured as aforesaid, holder 12 is also longitudinally fixed in tray 10. Since the openings between the ribs 14b, 14c at the bottom of the tray are square, each holder 12 could also be turned 90° and clamped to the transverse ribs 14c of tray 10 if that were necessary to retain a particular instrument or device within the tray.

Of course the holder 12 need not extend the full width of tray 10. FIG. 4B illustrates a holder 70 which is similar to holder 12 expect that it is narrower so that it spans only two openings in the tray bottom.

FIG. 4C shows another holder 72 which is similar to holder 70 expect that its base is formed with a pair of integral depending posts 74 which are spaced apart a distance substantially equal to the diameter of the ribs comprising tray 10. When the holder 72 is clipped to tray 10 in a manner similar to that of holder 12 therein, the posts 74 will straddle a longitudinal rib 14b thereby positively fixing the lateral or transverse position of the holder within the tray even though the holder has resilient legs.

FIG. 4D illustrates a holder 76 with a pair of spaced-apart upstanding loops 76a for fixating a relatively wide instrument or device, while FIG. 4E illustrates a holder 78 having a single upstanding loop 78a which may be suitable, for example, to secure a scissor handle or other such instrument having an eye.

Figure 5A:
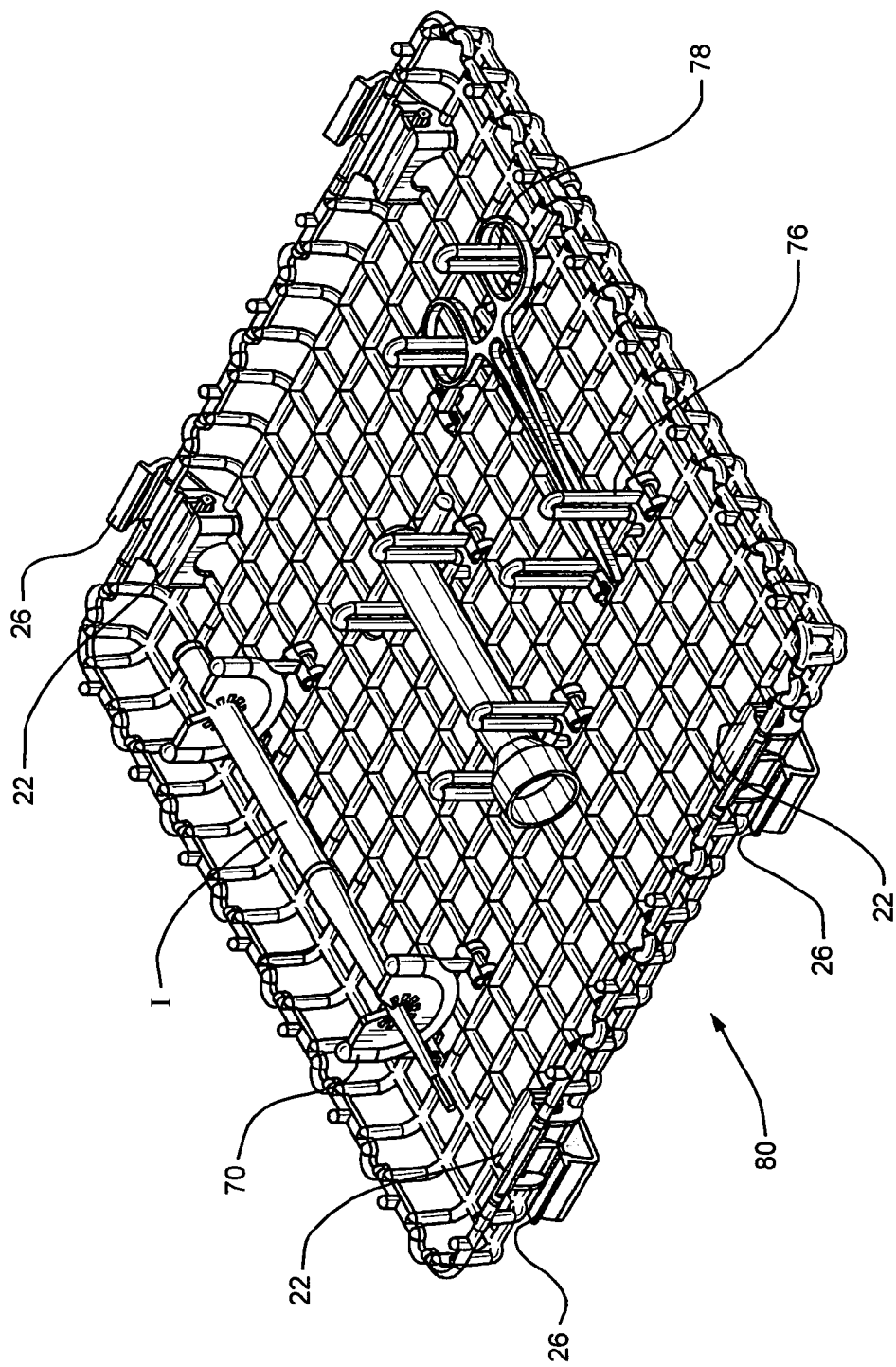
FIG. 5A is a view similar to FIG. 1 of another container system embodiment.
Figure 5B:
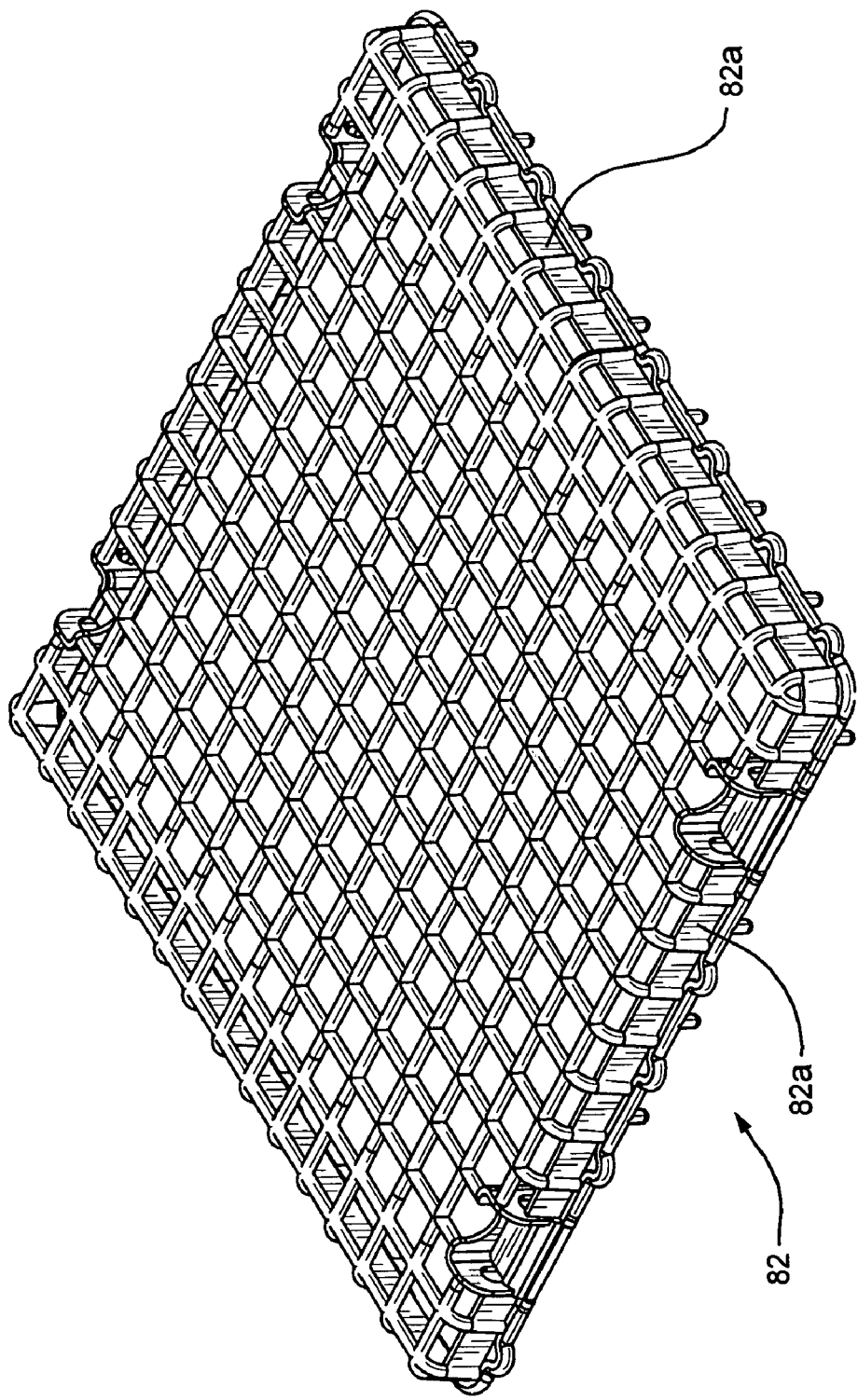
FIG. 5B is a perspective view of a cover that may be included in the FIG. 5A system.

Refer now to FIGS. 5A and 5B which illustrate, respectively, a molded plastic reticulated tray 80 and a cover 82 therefor with are much wider than tray 10 and cover 30 so that, using a variety of the instrument holders shown in FIGS. 4A to 4E, a whole set of instruments or devices can be protectively enclosed for sterilization and handling. Being larger, the tray 80 and cover 82 are formed with two sets of fixtures similar to fixtures 22 which may accommodate two sets of latch members similar to members 26 in FIG. 1. Here also, the tray 80 and cover 82 may be identical molded plastic parts. However, the illustrated cover 82 is somewhat different from the tray in that it includes solid side straps 82a to prevent loose instrument I from sliding out of the tray. As in FIG. 2, the latch members are attached to the tray fixtures 22 but not to the cover fixtures, with the latter functioning as keepers for the tray latches. Of course in both system embodiments, the latch members could just as well be hinged to the cover fixtures with the tray fixtures functioning as keepers for those latch members.

It is apparent from the foregoing that my container system has definite advantages in terms of protecting the instruments contained therein as well as facilitating efficient washing and sterilization of those instruments as well as the inside surfaces of the container. Yet being molded entirely of plastic, the system can be made in quantity relatively inexpensively. Therefore, it should prove to be very useful in hospital, clinics and other settings where medical instruments and devices have to be cleaned on a routine basis.

It will thus be seen that the objects set forth above, among those made apparent from the preceding description, are efficiently attained. Also, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

The invention claimed is:
1. A container system for medical instruments, the system comprising:
    a molded plastic reticulated tray having;
        a tray rim, formed from a continuous rib, wherein the molded plastic reticulated tray rim forms a perimeter of the molded plastic reticulated tray;

a tray wall, formed from a plurality of ribs connected to the tray rim, the plurality of ribs having opposite ends connected to the tray rim at spaced apart locations therealong; and a middle portion of the plurality of ribs forming a tray base, the tray base having a plurality of perpendicularly intersecting ribs formed from the plurality of ribs, the intersecting ribs having a circular cross-section and central axes configured in a plane, said intersecting ribs being dished and defining relatively large openings therebetween whereby a fluid sterilant directed at the plurality of perpendicularly intersecting ribs from the outside, upon flowing through said openings, will follow and contact rounded surfaces to the tray interior so that those surfaces are cleaned.

2. The container system of claim 1, wherein the total area of said openings is at least twice the total longitudinal-sectional area of said plurality of intersecting ribs.

3. The container system of claim 1, wherein the molded plastic reticulated tray is molded of polyphenylsulphone.

4. The container system of claim 1, wherein the molded plastic reticulated tray is generally rectangular and said openings are square.

5. The container system of claim 1, wherein the molded plastic reticulated tray includes at least two similar latch fixtures affixed to the continuous rib opposite and facing away from one another, each latch fixture including a journal bearing and a keeper surface.

6. The container system of claim 5, further including a latch member hinged to each latch fixture at the journal bearing thereof.

7. The container system of claim 1, and further including a reticulated cover which is a mate to said molded plastic reticulated tray so that when the reticulated cover is inverted and positioned with its continuous rim in register with the continuous rim of the molded plastic reticulated tray, the molded plastic reticulated tray and the reticulated cover make line contact and form a cage.

8. The container system of claim 7, further comprising a clamping mechanism for releasably clamping together the continuous rims of the molded plastic reticulated tray and the reticulated cover.

9. The container system of claim 8, wherein the clamping mechanism comprises a plurality of similar first latch fixtures affixed to the continuous rib of the molded plastic reticulated tray, said first latch fixtures being opposite and facing away from one another, a plurality of second latch fixtures affixed to the continuous rib of the reticulated cover, said second latch fixtures being opposite and facing away from one another, each of said latch fixtures including a journal bearing and a keeper surface, said first and second latch fixtures being located directly opposite one another when the continuous ribs of the molded plastic reticulated tray and the reticulated cover are in register with one another, said opposite latch fixtures constituting a cooperating pair of latch fixtures, and a latch member hinged to one of each cooperating pair of latch fixtures at the journal bearing thereof, each said latch member being adapted to engage the keeper surface of the other latch fixture of each cooperating pair of latch fixtures.

10. The container system of claim 1, further comprising at least one instrument holder, having at least one resilient leg, the at least one instrument holder releasably connected to different ones of said plurality of perpendicularly intersecting ribs and spanning at least one of said openings, wherein the at least one resilient leg is disposed substantially perpendicular to the plane of said intersecting ribs.

11. The container system of claim 10, wherein the at least one instrument holder includes a pair of spaced-apart flexible, resilient legs having free ends terminated by mirror image clips, each clip being adapted to engage around different ones of said plurality of intersecting ribs when said legs are flexed.

12. The container system of claim 11, wherein the length of each clip is slightly less than the side length of each of said openings.

13. The container system of claim 12, wherein said at least one instrument holder also includes a plurality of spaced-apart depending posts which are adapted to straddle one of said plurality of perpendicularly intersecting ribs when the at least one instrument holder is releasably connected to said different ones of said plurality of perpendicularly intersecting ribs.

* * * * *

UNITED STATES PATENT AND TRADEMARK OFFICE
CERTIFICATE OF CORRECTION

PATENT NO. : 8,349,271 B2
APPLICATION NO. : 11/369428
DATED : January 8, 2013
INVENTOR(S) : Riley Page 1 of 1

It is certified that error appears in the above-identified patent and that said Letters Patent is hereby corrected as shown below:

In the Claims:

Col. 6, Claim 1, Line 66, before "tray", delete "molded plastic reticulated".

Signed and Sealed this
Fourteenth Day of May, 2013

Teresa Stanek Rea
*Acting Director of the United States Patent and Trademark Office*